(12) United States Patent
Kishimoto et al.

(10) Patent No.: US 7,675,043 B2
(45) Date of Patent: Mar. 9, 2010

(54) MESH AND METHOD OF OBSERVING RUBBER SLICE TECHNICAL FIELD

(75) Inventors: Hiroyuki Kishimoto, Hyogo (JP); Hirofumi Nakamae, Hyogo (JP); Marina Kotani, Hyogo (JP); Hidehiko Dohi, Hyogo (JP); Hiroshi Jinnai, Kyoto (JP); Takeshi Kaneko, Kyoto (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 348 days.

(21) Appl. No.: 11/905,803

(22) Filed: Oct. 4, 2007

(65) Prior Publication Data

US 2008/0083884 A1 Apr. 10, 2008

(51) Int. Cl.
  *G21K 5/10* (2006.01)
(52) U.S. Cl. .............................. 250/442.11; 250/440.11; 250/443.1
(58) Field of Classification Search ............. 250/442.11
  See application file for complete search history.

(56) References Cited

U.S. PATENT DOCUMENTS 5,606,168 A * 2/1997 Chiron et al. ............. 250/443.1
7,034,316 B2 * 4/2006 Wagner et al. ......... 250/440.11
7,375,325 B2 * 5/2008 Burkhardt et al. ........... 250/307

FOREIGN PATENT DOCUMENTS

JP  11-329325 A  11/1999

* cited by examiner

*Primary Examiner*—David A. Vanore
*Assistant Examiner*—Phillip A. Johnston
(74) *Attorney, Agent, or Firm*—Birch, Stewart, Kolasch & Birch, LLP

(57) ABSTRACT

Left and right sides of the mesh sandwiching the placing region therebetween are set as left and right to-be-fixed portions to be fixed to sample holder separation portions respectively to be moved in a stretch direction. A slit for dividing use is formed from a portion of the periphery of the mesh disposed between the left and right to-be-fixed portions thereof toward the rubber slice-placing position of the mesh in a direction orthogonal to the stretch direction of the rubber slice or a direction inclined thereto. When the to-be-fixed portions are moved in a separation direction by moving the sample holder separation portions, the mesh is divided into left and right parts by the slit for dividing use so that the rubber slice fixed to the left and right sides of the mesh is stretched.

8 Claims, 8 Drawing Sheets

[Prior Art]

[Prior Art]

MESH AND METHOD OF OBSERVING RUBBER SLICE TECHNICAL FIELD

This nonprovisional application claims priority under 35 U.S.C. § 119(a) on Patent Application No(s). 2006-275543 filed in Japan on Oct. 6, 2006, the entire contents of which are hereby incorporated by reference.

FIELD OF THE INVENTION

The present invention relates to a mesh for holding a sample when the sample is observed by a microscope and a method of observing a rubber slice used as the sample by holding the rubber slice by the mesh, and more particularly to a mesh capable of observing a rubber slice in a stretch process and the rubber slice both in the stretch process and a contraction process.

In observing a sample with a microscope such as a transmissive electron microscope (TEM), after the sample is thinned with a cutting device, the thinned sample is fixed to a sample-supporting material called a mesh. After the mesh is fixed to the exclusive sample holder, the sample is observed.

Normally, a disk-shaped mesh 1 having a diameter of about 3 mm has reticulate openings 2, narrow groove-shaped openings 3, and a single hole 4 as shown in FIG. 10 so that the mesh 1 is capable of transmitting electron beams therethrough. As shown in FIG. 11, a thinned sample 4 is fixed to an upper surface of a central portion of the mesh 1 having openings 3 formed therethrough.

It is necessary to thin the sample to such an extent that the sample is capable of transmitting electron beams therethrough. It is known that the sample is thinned by using a device called a microtome and that a specific portion of the sample is thinned by using a focused ion beam processing method (FIB processing). In Japanese Patent Application Laid-Open No. 11-329325, a mesh having a specific configuration suitable for the FIB processing is proposed.

When the sample is made of rubber, observing a rubber slice undergoing a stretch process and the rubber slice undergoing the stretch process and thereafter a contraction process (return step) is useful for analyzing breakage, damage, deterioration, and wear of rubber and the mechanism of the generation of hysteresis loss and is also useful for making a combined design based on these analyses.

It is almost impossible to stretch a conventional mesh to which the sample is fixed, which makes it impossible to observe the rubber slice in a stretched state. Even though the mesh is forcibly stretched, it has a slight stretched amount and remains deformed as a result of the stretching. Thus it is impossible to return the rubber slice stretched on the mesh to its original state and observe the rubber slice in the contraction process (return step).

Patent document: Japanese Patent Application Laid-Open No. 11-329325

SUMMARY OF THE INVENTION

The present invention has been made in view of the above-described problems. It is an object of the present invention to provide a mesh allowing a rubber slice to be observed in a stretch process and in addition both in the stretch process and a contraction process and a method of observing the rubber slice by using the mesh.

To solve the above-described problem, the first invention provides a mesh supporting a rubber slice in a stretch process so that the rubber slice can be observed by a microscope, wherein an upper surface of a central portion of the mesh is set as a placing region to which the rubber slice is fixed; left and right sides of the mesh sandwiching the placing region therebetween are set as left and right to-be-fixed portions to be fixed to sample holder separation portions respectively to be moved in a stretch direction; and a slit for opening use is formed by cutting the mesh in a required length from an outer edge thereof disposed between the left and right to-be-fixed portions in a direction orthogonal to the stretch direction or a direction inclined thereto. In this construction, when the to-be-fixed portions are moved in a separation direction by moving the sample holder separation portions, the slit for opening use is opened toward the outer edge of the mesh to stretch the mesh in the stretch direction so that the rubber slice, left and right sides of which have been fixed to the to-be-fixed portions respectively is stretched.

In the above-described construction, the slit for opening use is formed by cutting the mesh in the required length from a portion of its periphery disposed between its left and right to-be-fixed portions in the direction orthogonal to the stretch direction or the direction inclined thereto. Therefore by separating the sample holder separation portions to which the left and right sides of the mesh have been fixed respectively from each other and moving the sample holder separation portions in the stretch direction, the mesh is uniformly stretched in the stretch direction while the slits for opening use is being opened, and the rubber slice fixed to the mesh is also stretched, as the mesh is stretched. Accordingly by only moving the sample holder separation portions to which the left and right sides of the mesh have been fixed in the stretch direction, it is possible to stretch the rubber slice at any desired degree of stretching and directly observe the state of the rubber slice at any desired degree of stretching. Thereby it is possible to observe the change of the state (morphology change) of the rubber slice in the stretch process.

The dimension, position, number, and cutting direction of each slit for opening use is not restricted specifically respectively, provided that the rubber slice on the mesh can be stretched by extending the mesh in the stretch direction, but appropriately set according to the configuration of the opening of the mesh, the configuration of the rubber slice fixed onto the mesh, and the fixing position of the rubber slice.

But to allow the slits for opening use to be uniformly extended in the left-to-right direction about the center of the mesh, it is preferable that the left side of the slit for opening use and the right side thereof are disposed symmetrically with respect to the center of the mesh. To extend the mesh in the stretch direction by opening the slit for opening use, it is preferable to form a plurality of the slits for opening use from upper and lower outer edges of the mesh with the upper and lower slits for opening use alternating with each other.

The second invention provides a mesh supporting a rubber slice in a stretch process and a contraction process so that the rubber slice can be observed by a microscope. An upper surface of a central portion of the mesh is set as a placing region, having an opening, to which the rubber slice is fixed; left and right sides of the mesh sandwiching the placing region therebetween are set as left and right to-be-fixed portions to be fixed to sample holder separation portions to be moved in a stretch direction; and a slit for dividing use is formed by cutting the mesh from an outer edge thereof disposed between the left and right to-be-fixed portions toward the rubber slice-placing region in a direction orthogonal to the stretch direction or a direction inclined thereto. In this construction, when the to-be-fixed portions are moved in a separation direction by moving the sample holder separation portions, the rubber slice, left and right sides of which have been fixed to the to-be-fixed portions respectively divided by the slit for dividing use is stretched; and when the to-be-fixed portions are moved from a stretched position in an approach direction by moving the sample holder separation portions, the rubber slice is contracted.

In the above-described construction, the mesh has the slit for dividing use formed from a portion of its periphery disposed between the left and right to-be-fixed portions of the mesh to be fixed to the sample holder separation portions respectively toward the rubber slice-placing position of the mesh in the direction orthogonal to the stretch direction of the rubber slice or the direction inclined thereto. Therefore by moving the sample holder separation portions which are provided on the sample holder and to which the left and right sides of the mesh have been fixed respectively in the stretch direction, the mesh is divided into the left and right parts in the stretch direction and moved away from each other. The rubber slice fixed to the left and right parts of the mesh is stretched uniformly in the stretch direction owing to the division of the mesh and move-away of the left and right parts thereof. Thus by only moving the sample holder separation portions to which the left and right sides of the mesh have been fixed respectively in the stretch direction, it is possible to stretch the rubber slice at any desired degree of stretching without deforming the mesh and directly observe the state of the rubber slice at any desired degree of stretching. Thereby it is possible to observe the change of the state (morphology change) of the rubber slice in the stretch process.

When the sample holder separation portions are moved in the contraction direction in which the left and right to-be-fixed portions are approached to each other, the divided left and right parts of the mesh approach to each other and finally can be restored to the original undivided state without the mesh remaining strained. Therefore it is possible to restore the rubber slice to the state before it is stretched and observe the state of the rubber slice not only in the stretch process but also in the contraction process (return process).

As described above, when the slit for dividing use is formed in the direction orthogonal to the stretch direction or the direction inclined thereto, it is possible to stretch the rubber slice in the stretch direction by dividing the mesh. But to form the slit for dividing use in the direction orthogonal to the stretch direction is simplest and allows the rubber slice to be uniformly stretched in the stretch direction.

When the slit for dividing use is formed by inclining it to the stretch direction, it is especially preferable to incline the slit for dividing use not less than 10 degrees to the stretch direction.

A reticulate opening or a narrow groove-shaped opening is formed in the rubber slice-placing region. The slit for opening use or the slit for dividing use is formed in a peripheral portion of the mesh surrounding the reticulate opening or the narrow groove-shaped opening by cutting the mesh from the outer edge thereof.

As described above, the mesh may have the reticulate opening or the narrow-groove-shaped opening formed at the rubber slice-placing position.

In the case of the mesh having the reticulate opening formed therethrough, unless the slit for opening use or the slit for dividing use is formed not only in the peripheral portion of the mesh constructing the peripheral frame thereof but also in the peripheral portion of thread surrounding the reticulate opening, it is often difficult to extend the mesh in the stretch direction or divide the mesh into the left and right parts by opening the slit for opening use.

In the case of the mesh having the narrow-groove-shaped opening formed therethrough, by forming one slit for opening use at each of upper and lower positions of the mesh sandwiching the narrow-groove-shaped opening therebetween, it is possible to greatly extend the mesh in the stretch direction.

The slit for dividing use is formed by traversing the placing region through the opening. For example, by only forming one slit for dividing use at the upper and peripheral portions of the mesh surrounding the narrow-groove-shaped opening, the mesh can be divided into left and right parts.

In forming the slit for dividing use through the mesh, when the mesh is moved in the stretch direction to divide it into the left and right parts, an opening is generated between the separated left and right parts of the mesh. Therefore the reticulate opening and the narrow-groove-shaped opening do not necessarily have to be formed in the placing region.

The mesh of each of the first and second inventions can be used especially preferably for a transmissive electron microscope (TEM) and a scan type electron microscope (SEM) and in addition for a scan type probe microscope (SPM), a laser microscope, and an optical microscope.

The third invention provides a method of observing a rubber slice, wherein the rubber slice fixed to the rubber slice-placing region of the mesh is stretched by moving the sample holder separation portions to which left and right sides of the mesh of the first invention have been fixed respectively in a stretch direction so that the rubber slice in a stretch process is observed by a microscope.

In the third invention, by using the mesh of the first invention through which the slit for opening use is formed by cutting the mesh, the rubber slice is stretched by opening the slit for opening use and extending the mesh in the stretch direction. Therefore as the mesh is extended, the mesh remains deformed to some extent. Thus the third invention is not suitable for observing the rubber slice in the contraction process but suitable for observing the rubber slice in the stretch direction.

The fourth invention provides a method of observing a rubber slice, wherein by moving sample holder separation portions to which left and right sides of the mesh of the second invention have been fixed respectively in a stretch direction, the rubber slice fixed to a rubber slice-placing region of the mesh is stretched to observe the rubber slice in a stretch process by a microscope, and thereafter by moving the sample holder separation portions in a contraction direction, the rubber slice fixed to the rubber slice-placing region of the mesh is contracted so that the rubber slice in a contraction process is observed by a microscope.

In the fourth invention, by dividing the mesh of the second invention through which the slit for dividing use is formed into two parts and moving the two parts away from each other, the rubber slice is stretched. Thus the mesh does not remain deformed. Therefore it is possible to observe the rubber slice not only in the stretch process but also in the contraction process (return process), which is useful for analyzing the breakage, damage, deterioration, and wear of rubber, the mechanism of reinforcing a polymer, a filler, and the like, and the analysis of the mechanism of the generation of hysteresis loss, and for making a combined design based on these analyses.

It is preferable to form the slit for opening use of the mesh and the slit for dividing use thereof used in the method of the third and fourth inventions of observing the rubber slice by cutting the mesh with razor, surgical knife, cutter or the like after the rubber slice is fixed to the upper surface of the central portion of the mesh. Thereby it is easy to handle the mesh because the mesh is not divided into a large number of pieces before the mesh is stretched and possible to fix the rubber slice to the mesh in a stable state.

As described above, according to the first invention, the slit for opening use is formed by cutting the mesh in the required length from the outer edge thereof disposed between its left and right to-be-fixed portions in the direction orthogonal to the stretch direction or the direction inclined thereto. Therefore by moving the sample holder separation portions to which the left and right sides of the mesh have been fixed respectively in the stretch direction, the mesh is uniformly stretched in the stretch direction while the slits for opening use is being opened, and the rubber slice fixed to the mesh is also stretched, as the mesh is stretched. Accordingly by moving the sample holder separation portions to which the left and right sides of the mesh have been fixed respectively in the stretch direction, it is possible to stretch the rubber slice at any desired degree of stretching and directly observe the state of the rubber slice, as the third invention provides.

According to the second invention, the mesh has the slit for dividing use formed from a portion of its periphery disposed between the left and right to-be-fixed portions of the mesh to be fixed to the sample holder separation portions respectively toward the rubber slice-placing position of the mesh in the direction orthogonal to the stretch direction of the rubber slice or the direction inclined thereto. Therefore by moving the sample holder separation portions to which the left and right sides of the mesh have been fixed respectively in the stretch direction, the mesh is divided into the left and right parts in the stretch direction. The rubber slice fixed to the left and right parts of the mesh is stretched uniformly in the stretch direction owing to the division of the mesh and the move-away of the left and right parts thereof. Thus by only moving the sample holder separation portions to which the left and right sides of the mesh have been fixed respectively in the stretch direction, it is possible to stretch the rubber slice at any desired degree of stretching without deforming the mesh and directly observe the rubber slice in the stretch process.

When the sample holder separation portions are moved in the contraction direction, the divided left and right parts of the mesh approach to each other and finally can be restored to the original undivided state without the mesh remaining strained. Therefore it is possible to restore the rubber slice to the state before it is stretched and observe the state of the rubber slice not only in the stretch process but also in the contraction process (return process), as the fourth invention provides.

DETAILED DESCRIPTION OF THE PREFERRED EMBODIMENTS

Figure 1:
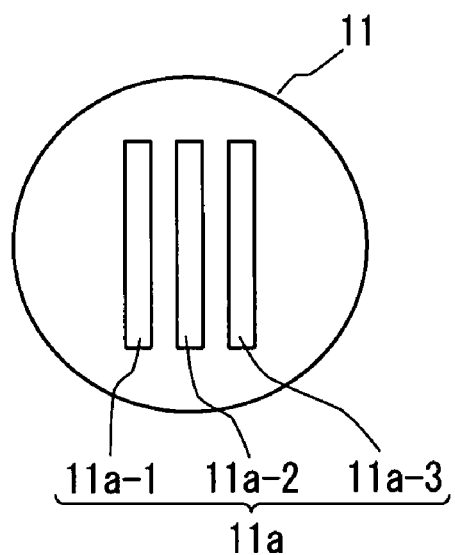
FIG. 1 is a schematic plan view showing a mesh of a first embodiment commercially available.

The embodiments of the present invention are described below with reference to the drawings.

FIGS. 1 through 5 show the first embodiment of the present invention.

A mesh 11 of the first embodiment has narrow groove-shaped openings 11a in a placing region 11b where a rubber slice 10 is placed and slits 12a, 12b for dividing use communicating with the narrow groove-shaped openings 11a.

Figure 2:
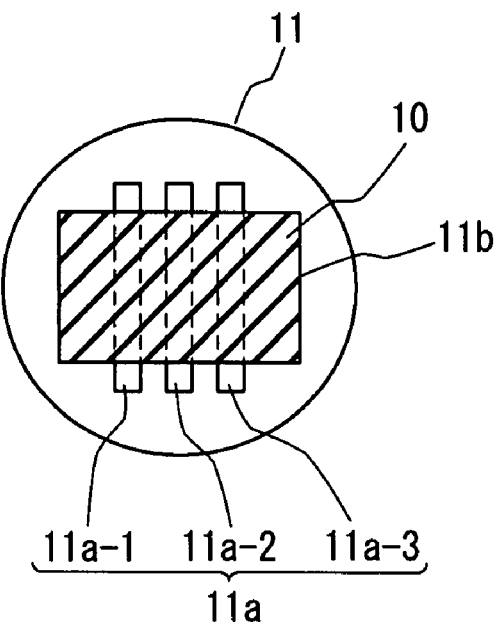
FIG. 2 is a schematic plan view showing a state in which a rubber slice is fixed to the mesh of FIG. 1.
Figure 3:
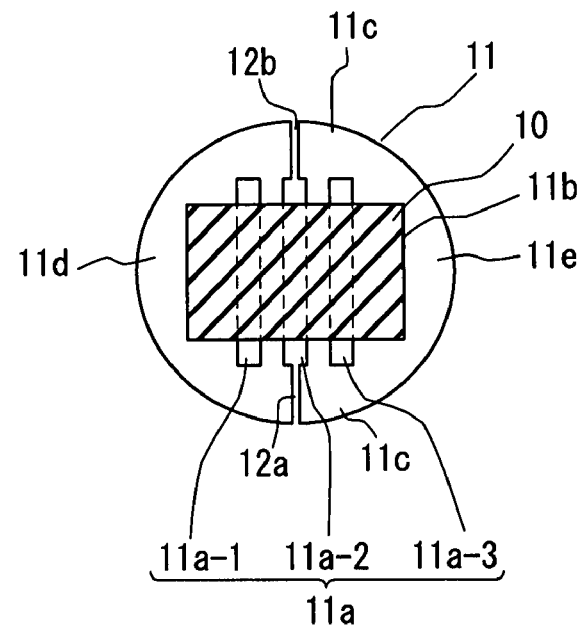
FIG. 3 is a schematic plan view showing a state in which a slit for dividing use is formed through the mesh by cutting it.
Figure 4:
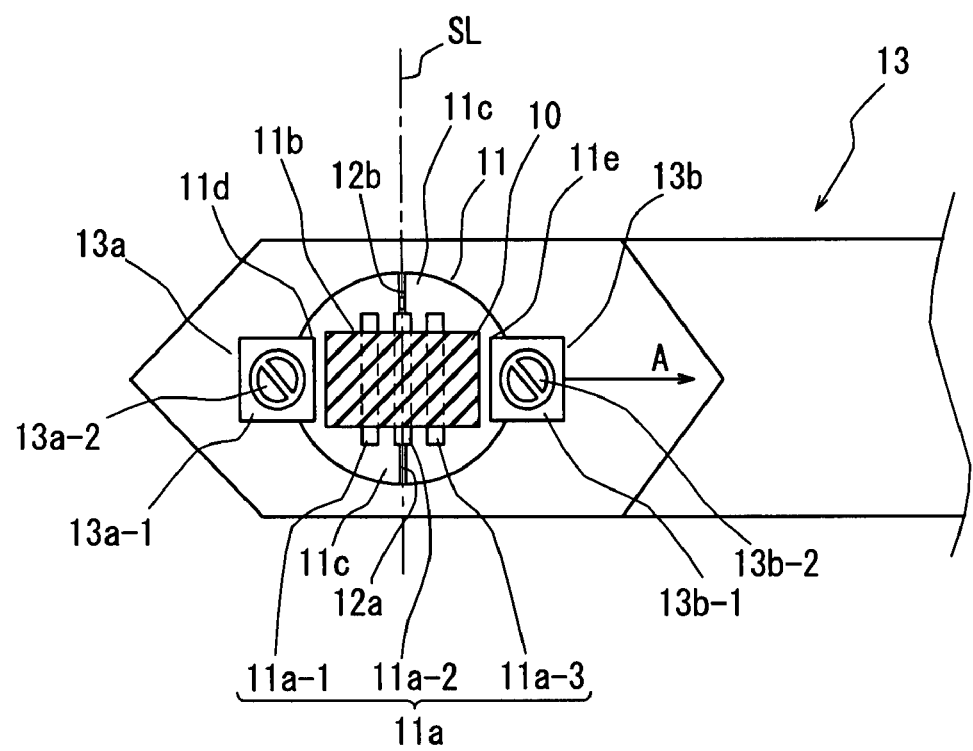
FIG. 4 is a schematic plan view showing a state in which the mesh is fixed to a sample holder.
Figure 5:
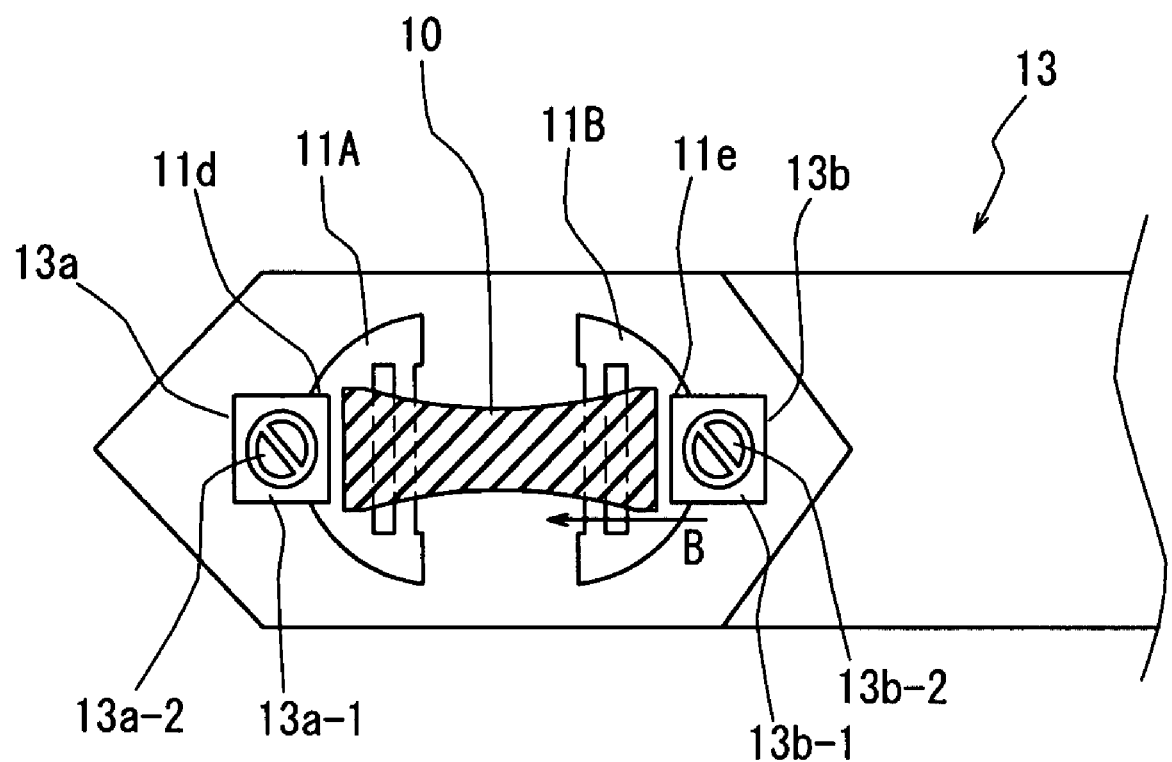
FIG. 5 is a schematic plan view showing a state in which the rubber slice is stretched by moving a sample holder separation portion.

That is, after the rubber slice 10 to be used as a sample shown in FIG. 2 is fixed to the mesh-placing region 11b disposed on an upper surface of the center of the mesh 11 which has three narrow groove-shaped openings 11a at the center thereof, as shown in FIGS. 3 and 4, the slits 12a, 12b for dividing use are sequentially formed on the mesh 11 by using a cutting blade (razor in the first embodiment).

Making detailed description, initially the thinned rubber slice 10 (1 mm (length)×2 mm (width)×200 nm (thickness)) is made from a rubber composition having components mixed at ratios shown in table 1 by using a microtome (not shown, commercial name: Ultramicrotome EM VC6, produced by LEICA Inc.).

The rubber slice 10 is placed on and fixed to the mesh-placing region 11b which is disposed on the upper surface of the center of the mesh 11 (diameter: 3 mm) which has the three narrow groove-shaped openings 11a (11a-1, 11a-2, and 11a-3) shown in FIG. 1 by using an exclusive loop (not shown) with the rubber slice 10 straddling over the three narrow groove-shaped openings 11a (FIG. 2).

TABLE 1

| Compounding components | Mixing amount (part by weight) |
|---|---|
| Styrene butadiene rubber | 100 |
| Carbon black (N220) | 70 |
| Sulfur | 1.5 |
| Zinc oxide | 3 |
| Accelerator B | 1 |

As shown in FIG. 4, the mesh 11 is placed on a sample holder 13. Both left and right sides (to-be-fixed portion 11d, 11e) of the mesh 11 are fixed to hold-down plates 13a-1, 13b-1 of sample holder separation portions 13a, 13b by screws 13a-2, 13b-2.

The slits 12a, 12b for dividing use are formed by cutting upper and lower centers of a peripheral frame 11c surrounding the narrow groove-shaped opening 11a of the mesh 11 in a direction orthogonal to a stretch direction (left-to-right direction) of the rubber slice 10 by using a cutting blade (not shown). In this manner, the mesh of the first embodiment is obtained.

That is, the slits 12a, 12b for dividing use are formed by cutting the peripheral frame 11c continually with the central opening 11a-2 of the three narrow groove-shaped openings 11a.

As described above, the slits 12a, 12b for dividing use are formed at the upper and lower peripheral portions of the central opening 11a-2 of the mesh 11. The slit 12a for dividing use, the opening 11a-2, and the slit 12b for dividing use are traversed through a placing portion where the rubber slice 10 is placed to form a division line SL. Thereby the mesh 11 is divided into left and right parts 11A, 11B.

The slits 12a, 12b for dividing use are located at the upper and lower positions in the drawings. Because the mesh 11 is horizontally disposed, the slits 12a, 12b for dividing use are located at front and rear sides of the horizontally disposed opening 11a-2.

As described above, the left and right parts 11A, 11B of the mesh 11 formed by dividing the mesh 11 at the division line SL formed as the boundary are fixed to the sample holder separation portions 13a, 13b respectively. Thus when the sample holder separation portions 13a, 13b are separated from each other by moving them in the stretch direction, the width of the division line SL gradually increases. As a result, the rubber slice 10 whose left and right sides have been fixed to the left and right parts 11A, 11B of the mesh 11 are stretched in the left-to-right direction in the drawing.

In the process of observing the rubber slice 10 with a microscope, the sample holder 13 to which the mesh 11 has been fixed is set on a transmissive electron microscope (not shown) (H7100 produced by Hitachi Co., Ltd., acceleration voltage 100 KV) to observe the rubber slice 10 having a degree of stretching at 0%.

Thereafter the rubber slice 10 is stretched by moving the sample holder separation portion 13b of both sample holder separation portions 13a, 13b to which the left and right sides 11d, 11e of the mesh 11 have been fixed respectively in the stretch direction (direction shown by an arrow A) to observe the rubber slice 10 having the degree of stretching at 50%, 100%, and 150% in a stretch process.

After the rubber slice 10 in the stretch process is observed, the left and right parts 11A, 11B of the mesh 11 are approached to each other by moving the sample holder separation portion 13b in a direction shown with an arrow B to contract the rubber slice 10 so that the rubber slice 10 having the degree of stretching at 100%, 50%, and 0% in a contraction process (return process) is observed.

As described above, the mesh 11 of the present invention has the slits 12a, 12b for dividing use formed from a portion of its periphery disposed between the left and right to-be-fixed portions 11d, 11e of the mesh 11 to be fixed to the sample holder separation portions 13a, 13b respectively toward the rubber slice-placing position 11b of the mesh 11 in the direction orthogonal to the stretch direction (left-to-right direction) of the rubber slice 10. Therefore by moving the sample holder separation portion 13b of the sample holder separation portions 13a, 13b to which the left and right sides 11d, 11e of the mesh 11 have been fixed respectively in the stretch direction (the direction shown by the arrow A), the mesh 11 is divided into the left and right parts 2A, 2B. The rubber slice 10 fixed to the left and right parts 2A, 2B of the mesh 11 is stretched uniformly in the stretch direction owing to the division and move-away of the mesh 11. Thus by only moving the sample holder separation portion 13b of the sample holder separation portions 13a, 13b to which the left and right sides 11d, 11e of the mesh 11 have been fixed respectively in the stretch direction, it is possible to stretch the rubber slice 10 at a desired degree of stretching without deforming the mesh 11 and directly observe the rubber slice 10 in the stretch process.

By moving the sample holder separation portion 13b in the contraction process (direction shown with an arrow B) subsequently to the stretch process, the left and right parts 2A, 2B of the mesh 11 formed by dividing the mesh 11 are approached to each other and finally can be restored to the original undivided state without the mesh 11 remaining strained. Therefore it is possible to restore the rubber slice 10 to the state before it is stretched and observe the state of the rubber slice 10 not only in the stretch process but also in the contraction process (return process).

The result of the observation of the rubber slice 10 in the stretch process and the contraction process (return process) is as described below.

That is, at 0% in the degree of stretching, the aggregation of a filler was observed. As the rubber slice 10 was stretched, initially, aggregated units of filler particles started to deform. When the degree of stretching exceeded 100%, deformation of each particle was observed. Separation was observed in a filler having a large stress concentration and on the interface of a polymer. It was also revealed that the filler did not stretch uniformly but stepwise changes occurred according to each strain.

When the degree of stretching was returned to 0% in the contraction process, a process of return to the original aggregated structure was observed.

Figure 6A:
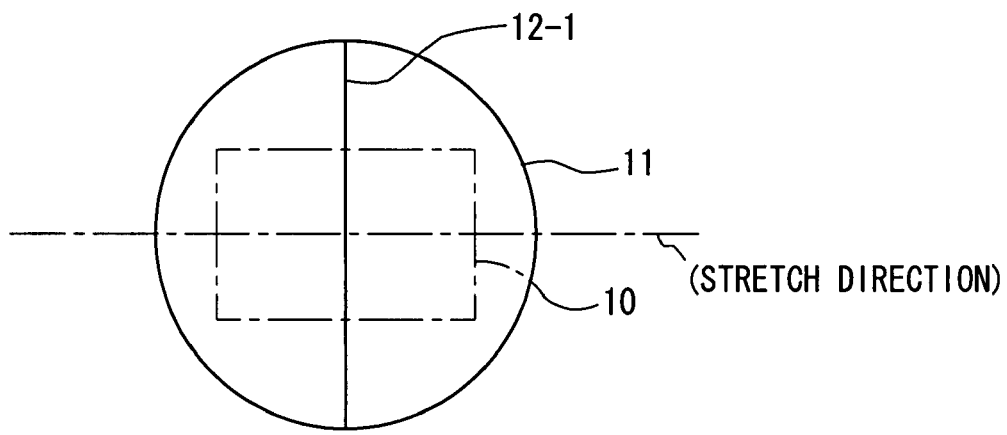
FIGS. 6(A) through 6(C) are plan views showing meshes of modifications of a first modification.
Figure 6B:
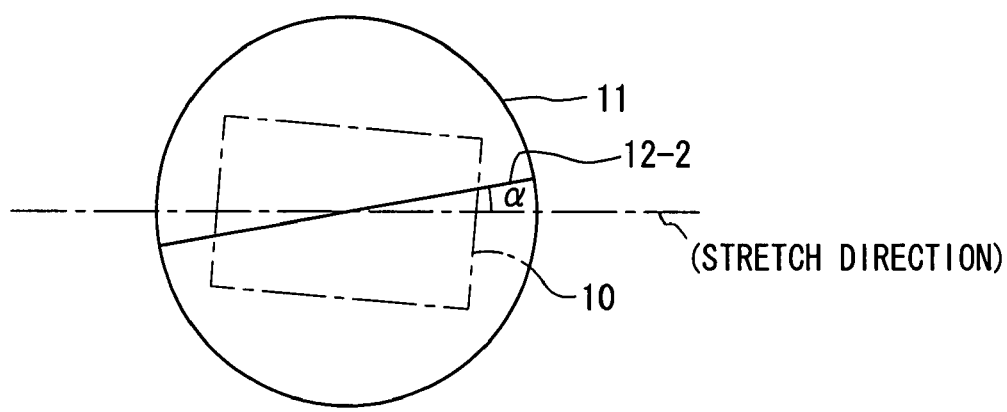
Figure 6C:
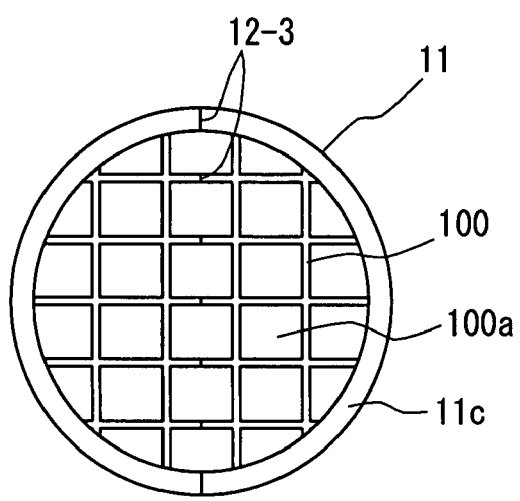

FIGS. 6(A) through 6(C) show modifications of the first embodiment.

In FIG. 6(A), an opening is not formed on the mesh 11 at the position where the rubber slice is placed, but only one slit 12-1 for dividing use is formed on the mesh 11 in the direction orthogonal to the stretch direction.

In FIG. 6(B), only one slit 12-2 for dividing use is formed on the mesh 11 by inclining it at an angle of α of 10 degrees to the stretch direction.

By providing the mesh 11 with the slit for dividing use, an opening is generated between divided parts of the mesh. Thus the opening does not necessarily have to be formed.

In the mesh 11 shown in FIG. 6(C), the peripheral frame 11c holds reticulate lines 100 consisting of fibers to form narrow groove-shaped openings 100a. In the mesh 11, slits 12-3 for dividing use are formed through the peripheral frame 11c and the reticulate lines 100.

Figure 7:
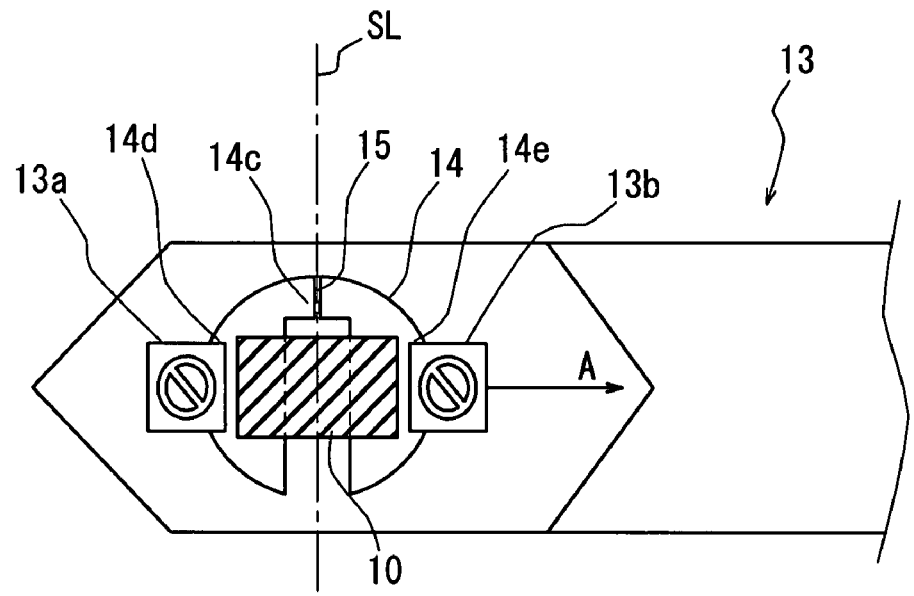
FIG. 7 is a schematic plan view showing a mesh of a second embodiment.

FIG. 7 shows a second embodiment.

A mesh 14 of the second embodiment has one narrow groove-shaped opening 14a formed by cutting a lower side of a peripheral frame 14c. One slit 15 for dividing use is formed at an upper side of the peripheral frame 14c to form the division line SL of the narrow groove-shaped opening 14a and the slit 15 for dividing use.

After left and right sides 14d, 14e of the mesh 14 are fixed to the sample holder separation portions 13a, 13b, respectively with the rubber slice 10 fixed to the mesh 14, the slit 15 for dividing use is formed in the direction orthogonal to the stretch direction (left-to-right direction).

In the second embodiment, by the movement of the sample holder separation portion 13b in the stretch direction, the mesh 14 is divided into left and right parts, and without deforming the mesh 14, the rubber slice 10 can be stretched uniformly in the stretch direction. Therefore similarly to the first embodiment, the rubber slice 10 in the stretch process and the contraction process (return process) can be observed.

Figure 8:
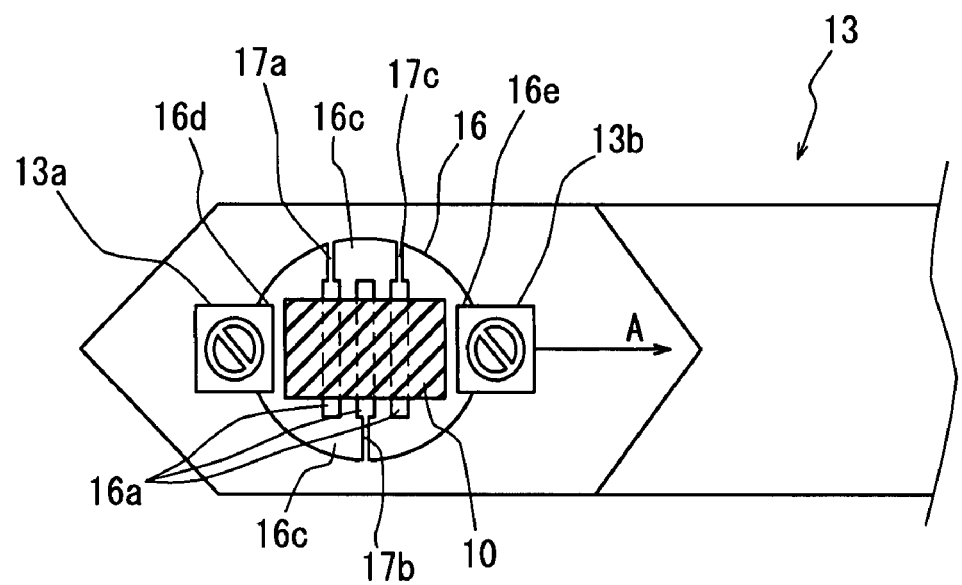
FIG. 8 is a schematic plan view showing a mesh of a third embodiment.

FIG. 8 shows a third embodiment.

In a mesh 16 of the third embodiment, slits 17a, 17b, and 17c for opening use are alternately formed at upper and lower positions of a peripheral frame 16c surrounding a narrow groove-shaped opening 16a in the direction orthogonal to the stretch direction (left-to-right direction) of the rubber slice 10 to such an extent that the slits 17a, 17b, and 17c for opening use do not communicate with the narrow groove-shaped opening 16a.

The slits 17a, 17b, and 17c for opening use are formed after the left and right sides 16d, 16e of the mesh 16 are fixed to the sample holder separation portions 13a, 13b respectively with the rubber slice 10 fixed to the mesh 16. Other constructions of the third embodiment are similar to those of the first embodiment.

According to the above-described construction, the mesh 11 has the slits 17a, 17b, and 17c for opening use formed vertically and alternately on the peripheral frame 16c disposed between the left and right to-be-fixed portions 16d, 16e of the mesh 16 to be fixed to the sample holder separation portions 13a, 13b respectively in the direction orthogonal to the stretch direction (left-to-right direction). Therefore by moving the sample holder separation portion 13b of the sample holder separation portions 13a, 13b to which the left and right sides 16d, 16e of the mesh 16 have been fixed respectively in the stretch direction (the direction shown by the arrow A), the mesh 16 is stretched in the stretch direction, while the slits 17a, 17b, and 17c for opening use are being opened, and the rubber slice 10 fixed to the mesh 16 is also stretched, as the mesh 16 is stretched.

Thus by only moving the sample holder separation portion 13b of the sample holder separation portions 13a, 13b to which the left and right sides 16d, 16e of the mesh 16 have been fixed respectively in the stretch direction, it is possible to stretch the rubber slice 10 at a desired degree of stretching and directly observe the rubber slice 10 in the stretch process.

When the sample holder separation portions 13a, 13b are moved to each other in the approach direction after they are moved away from each other in the stretch direction, the rubber slice 10 is strained unless the shrinkage factor of the mesh 16 and that of the rubber slice 10 are equal to each other. Therefore it is impossible to use the mesh 16 having the slit for opening use to observe the rubber slice 10 in the contraction process.

When the shrinkage factor of the mesh 16 having the slit for opening use is approximately equal to that of the rubber slice 10, the mesh 16 having the slit for opening use can be used in the contraction process.

Figure 9A:
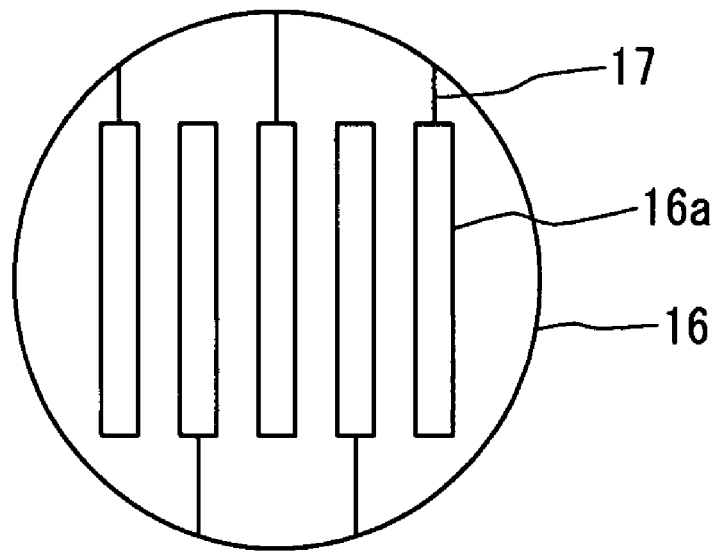
FIGS. 9(A) and 9(B) are plan views showing meshes of modifications of a third modification.
Figure 9B:
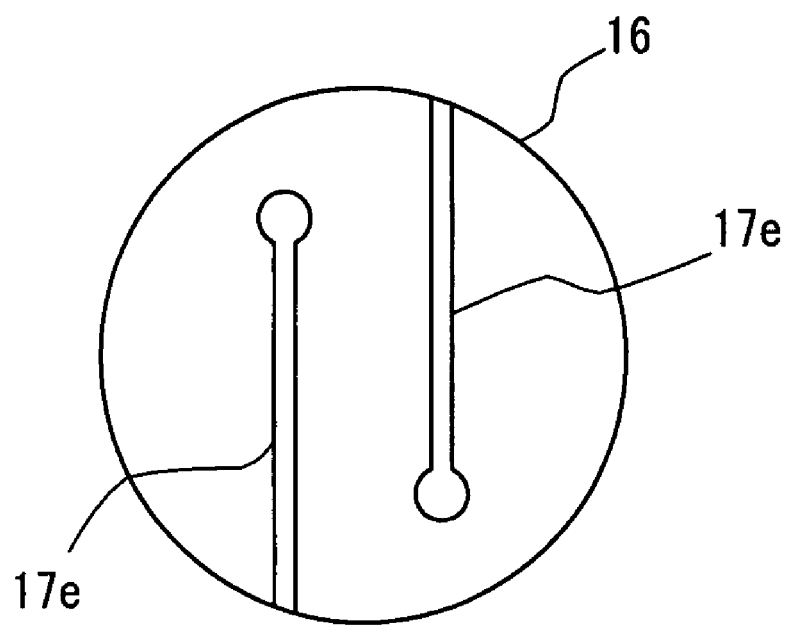
Figure 10A:
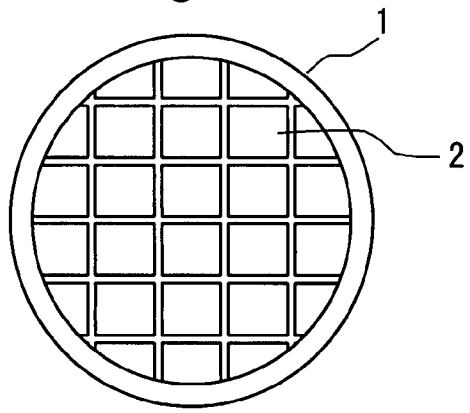
FIG. 10 shows a conventional art.
Figure 10B:
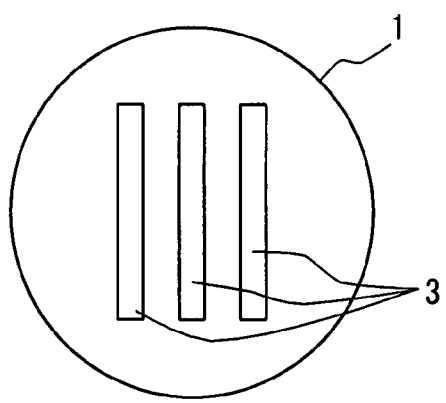
Figure 10C:
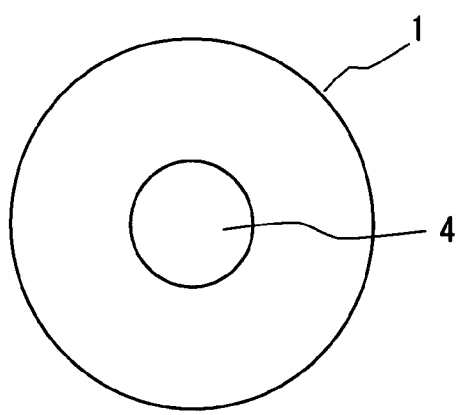
Figure 11:
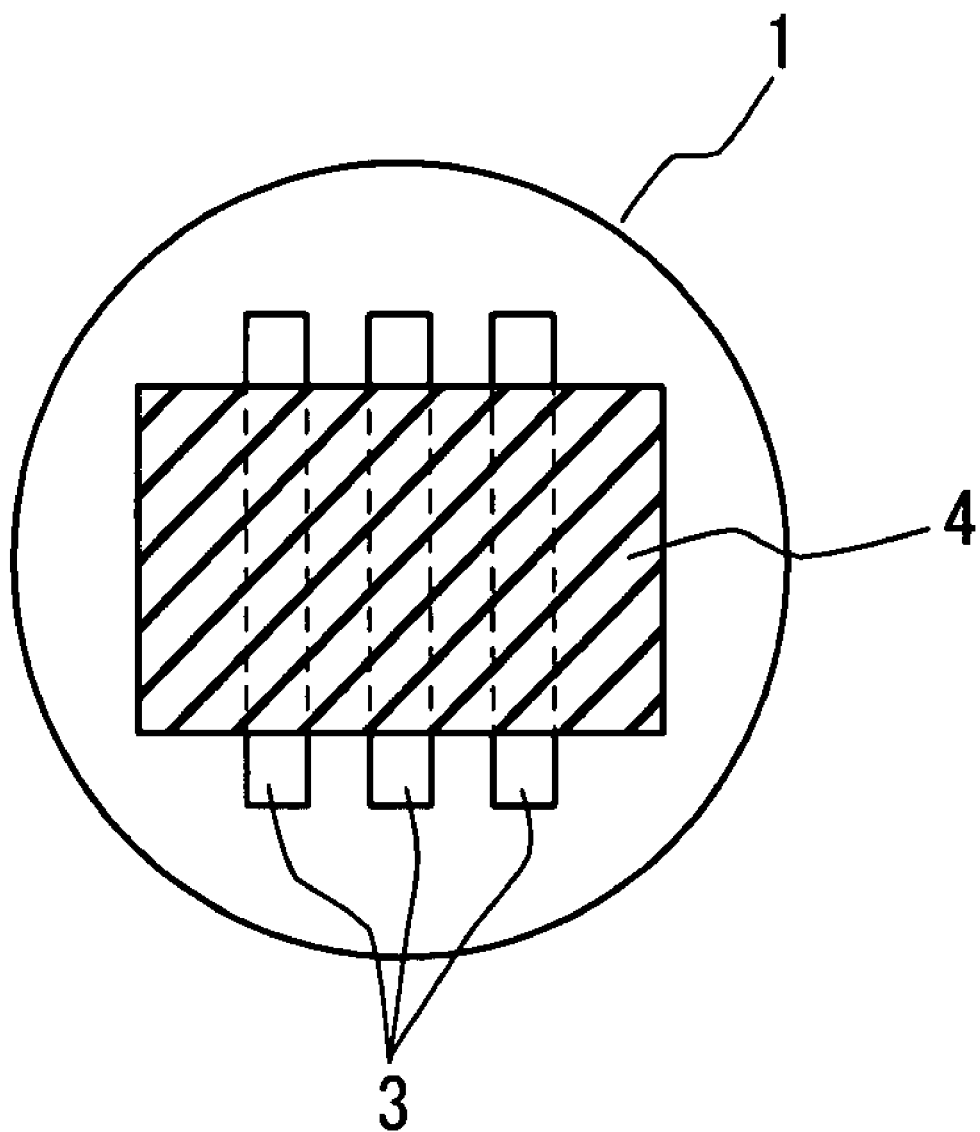
FIG. 11 shows a conventional art.

FIGS. 9(A) and 9(B) show modifications of the third embodiment.

In the mesh 16 of FIG. 9(A), a large number of narrow groove-shaped openings 16a is formed side by side in the central portion of the mesh 16 in the left-to-right direction, and slits for opening use 17 are formed alternately at upper and lower portions of the narrow groove-shaped openings 16a.

In the mesh 16 of FIG. 9(B), openings are not formed, but a slit for opening use 17e is formed by cutting the mesh 16 from an upper peripheral edge of the mesh 16, whereas a slit for opening use 17f is formed by cutting the mesh 16 from a lower peripheral edge of the mesh 16 with a sphere formed at a leading end of each of the slits 17e, 17f. By spherically forming the leading end thereof, it is possible to prevent the mesh 16 from being twisted when the mesh 16 is stretched.

In any of the above-described embodiments, after the rubber slice is fixed to the mesh, the slit is formed. But if the position where the slit for opening use is formed does not interfere with the region of the mesh 16 where the rubber slice 10 is placed, the slit may be formed through the mesh 16 before the rubber slice 10 is placed on and fixed to the mesh 16.

The mesh of the present invention is preferably used to hold the rubber slice in observing the state of the rubber slice in the stretch process and the contraction process. In addition to the rubber slice, the mesh of the present invention can be also used to observe a sample to be stretched, for example, a film made of resin in the stretch direction and the contraction process.

The mesh of the present invention is preferably used as a sample-holding material in observing a sample by a scan type electron microscope, a transmissive electron microscope, a scan type probe microscope, a laser microscope, and an optical microscope.

What is claimed is:

1. A mesh supporting a rubber slice in a stretch process so that said rubber slice can be observed by a microscope,
    wherein an upper surface of a central portion of said mesh is set as a placing region to which said rubber slice is fixed; left and right sides of said mesh sandwiching said placing region therebetween are set as left and right to-be-fixed portions to be fixed to sample holder separation portions respectively to be moved in a stretch direction; and a slit for opening use is formed by cutting said mesh in a required length from an outer edge thereof disposed between said left and right to-be-fixed portions in a direction orthogonal to said stretch direction or a direction inclined thereto,
    when said to-be-fixed portions are moved in a separation direction by moving said sample holder separation portions, said slit for opening use is opened toward said outer edge of said mesh to stretch said mesh in said stretch direction so that said rubber slice, left and right sides of which have been fixed to said to-be-fixed portions respectively is stretched.

2. A mesh supporting a rubber slice in a stretch process and a contraction process so that said rubber slice can be observed by a microscope,
    wherein an upper surface of a central portion of said mesh is set as a placing region, having an opening, to which said rubber slice is fixed; left and right sides of said mesh sandwiching said placing region therebetween are set as left and right to-be-fixed portions to be fixed to sample holder separation portions to be moved in a stretch direction; and a slit for dividing use is formed by cutting said mesh from an outer edge thereof disposed between said left and right to-be-fixed portions toward said rubber slice-placing region in a direction orthogonal to said stretch direction or a direction inclined thereto,
    when said to-be-fixed portions are moved in a separation direction by moving said sample holder separation portions, said rubber slice, left and right sides of which have been fixed to said to-be-fixed portions respectively divided by said slit for dividing use is stretched; and when said to-be-fixed portions are moved from a stretched position in an approach direction by moving said sample holder separation portions, said rubber slice is contracted.

3. The mesh according to claim 1, wherein a reticulate opening or a narrow groove-shaped opening is formed through said rubber slice-placing region of said mesh; and said slit for opening use or said slit for dividing use is formed through a peripheral portion of said mesh surrounding said reticulate opening or said narrow groove-shaped opening by cutting said mesh from said outer edge thereof.

4. The mesh according to claim 2, wherein a reticulate opening or a narrow groove-shaped opening is formed through said rubber slice-placing region of said mesh; and said slit for opening use or said slit for dividing use is formed through a peripheral portion of said mesh surrounding said reticulate opening or said narrow groove-shaped opening by cutting said mesh from said outer edge thereof.

5. The mesh according to claim 3, wherein said slit for dividing use is formed by traversing said placing region through said opening.

6. The mesh according to claim 4, wherein said slit for dividing use is formed by traversing said placing region through said opening.

7. A method of observing a rubber slice, wherein said rubber slice fixed to said rubber slice-placing region of said mesh is stretched by moving said sample holder separation portions to which left and right sides of said mesh according to claim 1 have been fixed respectively in a stretch direction so that said rubber slice in a stretch process is observed by a microscope.

8. A method of observing a rubber slice, wherein by moving sample holder separation portions to which left and right sides of said mesh according to claim 2 have been fixed respectively in a stretch direction, said rubber slice fixed to a rubber slice-placing region of said mesh is stretched so that said rubber slice in a stretch process is observed by a microscope, and thereafter by moving said sample holder separation portions in a contraction direction, said rubber slice fixed to said rubber slice-placing region of said mesh is contracted so that said rubber slice in a contraction process is observed by a microscope.

\* \* \* \* \*